United States Patent
Chen et al.

(10) Patent No.: US 9,636,368 B2
(45) Date of Patent: May 2, 2017

(54) **STRAIN OF *LACTOBACILLUS RHAMNOSUS* AND ITS METABOLITES FOR USE IN INHIBITING XANTHINE OXIDASE AND TREATING GOUT**

(71) Applicant: Food Industry Research and Development Institute, Hsinchu (TW)

(72) Inventors: Siao-Jhen Chen, Tainan (TW); Yen-Lin Chen, Hsinchu (TW); Hsun-Yin Hsu, Hsinchu (TW); Shy-Yunn Wann, Hsinchu (TW); Mei-Huei Chen, Hsinchu (TW); Li-Wen Yu, Hsinchu (TW)

(73) Assignee: Food Industry Research and Development Institute, Hsinchu (TW)

( * ) Notice: Subject to any disclaimer, the term of this patent is extended or adjusted under 35 U.S.C. 154(b) by 0 days.

(21) Appl. No.: 14/823,585

(22) Filed: Aug. 11, 2015

(65) Prior Publication Data

US 2016/0051602 A1    Feb. 25, 2016

Related U.S. Application Data

(60) Provisional application No. 62/040,616, filed on Aug. 22, 2014.

(51) Int. Cl.

| | |
|---|---|
| *A61K 35/747* | (2015.01) |
| *C12P 1/04* | (2006.01) |
| *C12N 1/20* | (2006.01) |
| *C12R 1/225* | (2006.01) |
| *C12N 9/02* | (2006.01) |
| *A23L 2/38* | (2006.01) |
| *A23L 33/135* | (2016.01) |
| *A61K 9/19* | (2006.01) |
| *C12N 1/02* | (2006.01) |
| *A61K 9/00* | (2006.01) |
| *A23L 2/52* | (2006.01) |

(52) U.S. Cl.
CPC ........... *A61K 35/747* (2013.01); *A23L 2/382* (2013.01); *A23L 33/135* (2016.08); *C12N 1/20* (2013.01); *C12N 9/0093* (2013.01); *C12P 1/04* (2013.01); *C12R 1/225* (2013.01); *A23L 2/52* (2013.01); *A61K 9/0095* (2013.01); *A61K 9/19* (2013.01); *C12N 1/02* (2013.01); *C12N 2500/72* (2013.01); *C12Y 117/03002* (2013.01)

(58) Field of Classification Search
None
See application file for complete search history.

(56) References Cited

U.S. PATENT DOCUMENTS

| | | | | |
|---|---|---|---|---|
| 3,582,728 | A * | 6/1971 | Thoma | G01N 27/225 361/286 |
| 5,749,832 | A * | 5/1998 | Vadgama | A61B 5/14865 600/345 |
| 2002/0022019 | A1 * | 2/2002 | Laulund | A61K 35/741 424/93.45 |
| 2004/0185032 | A1 * | 9/2004 | Burrell | A61K 31/135 424/93.45 |
| 2004/0208863 | A1 * | 10/2004 | Versalovic | A61K 35/744 424/115 |
| 2009/0136468 | A1 * | 5/2009 | Speelmans | A23L 1/3014 424/93.45 |
| 2010/0316618 | A1 | 12/2010 | Tsuboi et al. | |
| 2011/0014168 | A1 | 1/2011 | Tsuboi et al. | |
| 2012/0045422 | A1 * | 2/2012 | Crane | A23L 1/296 424/93.45 |
| 2013/0330299 | A1 | 12/2013 | Ranganathan | |

FOREIGN PATENT DOCUMENTS

| | | |
|---|---|---|
| CN | 102370859 A | 3/2012 |
| EP | 1649863 A1 | 4/2006 |
| EP | 2457576 A1 | 5/2012 |
| KR | 20130099653 A | 9/2013 |

OTHER PUBLICATIONS

Hashemzadeh, F et al. Effects of probiotics and antibiotic supplementation on serum biochemistry and intestinal microflora in broiler chicks. International Journal of Agriculture and Crop Sciences. 2013. 5(20): 2394-2398.*

Bouzaine, T et al. Adherence and colonization properties of Lactobacillus rhamnosus TB1, a broiler chicken isolate. Letters in Applied Microbiology. 2005. 40: 391-396.*

Austic, RE et al. Impaired renal clearnance of uric acid in chickens having hyperuricemia and articular gout. American Journal of Physiology. 1972. 223(3): 525-530.*

Izumida et al., "Hydroxyakalone, a Novel Xanthine Oxidase Inhibitor Produced by a Marine Bacterium, Agrobacterium auratiacum", J. Antibiotics 50:916-918.

* cited by examiner

*Primary Examiner* — Renee Claytor
*Assistant Examiner* — Susan E Fernandez
(74) *Attorney, Agent, or Firm* — Cesari and McKenna LLP

(57) ABSTRACT

A method for inhibiting xanthine oxidase and for reducing uric acid levels using a composition obtained by culturing *Lactobacillus rhamnosus* in a medium. Also disclosed is a composition including a metabolite of *Lactobacillus rhamnosus* for reducing uric acid levels in a subject and a method for producing the composition.

10 Claims, No Drawings ial Application Ser. No. 62/040,616, which was filed on Aug. 22, 2014. The content of that application is hereby incorporated by reference in its entirety.

STRAIN OF *LACTOBACILLUS RHAMNOSUS* AND ITS METABOLITES FOR USE IN INHIBITING XANTHINE OXIDASE AND TREATING GOUT

CROSS-REFERENCE TO RELATED APPLICATIONS

The present application claims the benefit of U.S. Provisional Application Ser. No. 62/040,616, which was filed on Aug. 22, 2014. The content of that application is hereby incorporated by reference in its entirety.

BACKGROUND

Field of the Invention

The invention relates to inhibition of xanthine oxidase activity by lactic acid bacteria and their fermentation metabolites.

Background Information

Uric acid is the end product of purine metabolism in the body. A high level of uric acid in the blood leads to the formation and deposition of uric acid crystals in the joints, kidneys, and other organs. A blood uric acid concentration higher than 7 mg/dL is considered to be hyperuricemia.

Hyperuricemia is a common metabolic disorder that is associated with gout, hypertension, cardiovascular disease, diabetes, and kidney disease. An epidemiological survey performed in Taiwan from 1993 to 2008 indicated that the percentage of male and female patients demonstrating hyperuricemia was 21.6% and 9.57%, respectively.

Xanthine oxidase is a key enzyme in the synthesis of uric acid. As a result, inhibition of xanthine oxidase activity can reduce the production of uric acid. Indeed, the xanthine oxidase inhibitor, uricase, is effective for lowering the concentration of uric acid in the blood. Uricase is an enzyme not found in humans. It is typically isolated as a recombinant mammalian protein and administered by IV infusion. As such, it can be expensive to produce and difficult to administer.

Allopurinol is also a xanthine oxidase inhibitor. This compound is administered clinically to lower serum uric acid levels. However, allopurinol has side effects, such as allergic reactions, gastrointestinal discomfort, leukopenia and thrombocytopenia, hepatitis, nephropathy, and 6-mercaptopurine toxicity, which in certain cases can lead to death.

In view of the drawbacks of existing therapies for hyperuricemia, many biopharmaceutical companies focused on the development of new uric acid-lowering agents. For example, Izumida et al., J. Antibiotics 50:916-918, isolated a compound that can lower uric acid levels, namely, hydroxyakalone, from the marine bacterium *Agrobacterium aurantiacum*.

Other microbial species have also been shown to possess uric-acid lowering capability, including strains of *Lactobacillus fermentum*, *Lactobacillus pentosus*, *Lactobacillus gasseri*, *Lactobacillus oris*, *Bifidobacterium longum*, and *Saccharomyces cerevisiae*. See, e.g., US Patent Application Publications 2010/0316618, 2011/0014168, and 2013/0330299; and European Patent Application Publications 2457576 and 1649863.

The need still exists to develop new xanthine oxidase inhibitors from natural sources which can be easily produced and safely administered.

SUMMARY

To meet this need, inhibitors of xanthine oxidase produced by lactic acid bacteria are provided.

A method for inhibiting xanthine oxidase is also provided. The method includes the steps of culturing *Lactobacillus rhamnosus* in a medium to form a composition and contacting the xanthine oxidase with the composition.

Also disclosed is a method for reducing uric acid levels in a subject. The method includes culturing *Lactobacillus rhamnosus* in a medium to form a composition and administering the composition to a subject having elevated uric acid levels. The amount administered is effective for reducing uric acid levels.

Within the scope of the invention is a method for producing a composition for reducing uric acid levels in a subject. The method is carried out by inoculating a medium with *Lactobacillus rhamnosus* and culturing the *Lactobacillus rhamnosus* in the medium to form a composition.

Further disclosed is a composition for reducing uric acid levels in a subject. The composition includes a metabolite of *Lactobacillus rhamnosus*.

The details of one or more embodiments of the invention are set forth in the description and the examples below. Other features, objects, and advantages of the invention will be apparent from the detailed description of several embodiments and also from the claims. All publications and patent documents cited herein are incorporated by reference in their entirety.

DETAILED DESCRIPTION

As mentioned above, a method is disclosed for reducing uric acid levels in a subject by administering a composition containing *Lactobacillus rhamnosus*. In a particular embodiment, the *Lactobacillus rhamnosus* is *Lactobacillus rhamnosus* I21 deposited under Accession No. DSM 28876.

In one embodiment, the subject is hyperuricemic. In another embodiment, the subject suffers from gout.

The method, as set out supra, includes a step of forming a composition by culturing *Lactobacillus rhamnosus* in a medium. The medium can be, but is not limited to, de Man-Rogosa-Sharpe (MRS) broth, milk, and juice. In specific embodiments, the medium is grape juice, mango juice, or orange juice. In a particular embodiment, the method includes a step of removing the *Lactobacillus rhamnosus* from the medium after culturing and prior to administering the composition.

The composition described above can be administered topically or systemically by routes including, but not limited to, intramuscular, intradermal, intravenous, subcutaneous, intraperitoneal, intranasal, oral, mucosal, and external.

Depending upon the route of administration, the composition can be formulated in various ways. For example, the composition can be a liquid solution, a suspension, an emulsion, a syrup, a tablet, a pill, a capsule, a sustained release formulation, a powder, a granule, an ampoule, an injection, an infusion, a kit, an ointment, a lotion, a liniment, a cream, or a combination thereof. The composition can be sterilized or mixed with a pharmaceutically acceptable carrier or excipient.

The term "carrier" or "excipient" as used herein refers to any substance, not itself a therapeutic agent, used as a carrier, diluent, adjuvant, or vehicle (i) for delivery of a therapeutic agent to a subject, (ii) for adding to a formulation to improve its handling or storage properties, and/or (iii) to facilitate formation of a dosage unit of the composition into a discrete article such as a capsule or tablet suitable for oral administration.

Suitable carriers or excipients are well known in the art of manufacturing pharmaceutical formulations or food products. Carriers or excipients can include, by way of illustration and not limitation, buffers, diluents, disintegrants, binding agents, adhesives, wetting agents, polymers, lubricants, glidants, substances added to mask or counteract a disagreeable taste or odor, flavors, dyes, fragrances, and substances added to improve appearance of the composition.

Acceptable carriers or excipients include citrate buffer, phosphate buffer, acetate buffer, bicarbonate buffer, stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, cellulosic materials (e.g., cellulose esters of alkanoic acids and cellulose alkyl esters), low melting wax cocoa butter, amino acids, urea, alcohols, ascorbic acid, phospholipids, proteins (e.g., serum albumin), ethylenediamine tetraacetic acid (EDTA), dimethyl sulfoxide (DMSO), sodium chloride or other salts, liposomes, mannitol, sorbitol, glycerol or powder, polymers (e.g., polyvinyl-pyrrolidone, polyvinyl alcohol, and polyethylene glycols), and other pharmaceutically acceptable materials. The carrier does not destroy the pharmacological activity of the therapeutic agent and is non-toxic when administered in doses sufficient to deliver a therapeutic amount of the agent.

The amount of the composition administered is effective for reducing uric acid levels in the subject. A skilled artisan can easily determine the effective amount by, e.g., measuring changes in the concentration of uric acid in the blood of the subject.

The method for inhibiting xanthine oxidase described above includes the step culturing *Lactobacillus rhamnosus* in a medium to form a composition. In a preferred embodiment, the *Lactobacillus rhamnosus* is *Lactobacillus rhamnosus* I21 deposited under Accession No. DSM 28876.

The medium can be, but is not limited to, de Man-Rogosa-Sharpe (MRS) broth, milk, and juice. In specific embodiments, the medium is grape juice, mango juice, or orange juice. In a particular embodiment, the method includes a step of lyophilizing the composition to form a powder.

The method for inhibiting xanthine oxidase also includes a step of contacting the xanthine oxidase with the composition described above. In one embodiment, the contacting step can be performed in vitro. For example, a preparation of xanthine oxidase can be placed in a vessel together with the composition. In an embodiment, the contacting step is performed by administering the composition orally to a subject having xanthine oxidase.

Summarized above is a method for producing a composition for reducing uric acid levels in a subject. The composition is produced by first inoculating a medium with *Lactobacillus rhamnosus*. In a specific embodiment, the *Lactobacillus rhamnosus* is *Lactobacillus rhamnosus* I21 deposited under Accession No. DSM 28876.

The medium for inoculating the *Lactobacillus rhamnosus* can be, but is not limited to, de Man-Rogosa-Sharpe (MRS) broth, milk, and juice. In certain embodiments, the medium is grape juice, mango juice, or orange juice.

After inoculating the medium with *Lactobacillus rhamnosus*, the inoculated media is subjected to culturing, thereby forming the composition for reducing uric acid levels in a subject. The culturing step can be carried out at 37° C. Additionally, the culturing step can be carried out under facultative anaerobic conditions. In an embodiment, the culturing is performed for 2 days.

The composition obtained by culturing *Lactobacillus rhamnosus* in a medium can be sterilized by methods including but not limited to pasteurization, irradiation, autoclave, and filtration. For example, the composition can be sterilized by filtration through a 0.2 μm filter. In a particularly preferred embodiment, the sterilized liquid broth is first filtered or centrifuged to remove the bacteria and then concentrated.

The method for producing a composition for reducing uric acid levels in a subject can include a step of removing the *Lactobacillus rhamnosus* from the composition. The *Lactobacillus rhamnosus* can have a cell density of $1 \times 10^8$ to $1 \times 10^9$ cells/ml prior to the removing step. In a preferred embodiment, the *Lactobacillus rhamnosus* cell density prior to removing them is $1 \times 10^9$ cells/ml.

In another embodiment, the method includes a step of lyophilizing the composition to form a powder.

The composition described above for reducing uric acid levels in a subject includes a metabolite of *Lactobacillus rhamnosus*. The metabolite is an inhibitor of xanthine oxidase activity. In a particular embodiment, the metabolite can be a metabolite of *Lactobacillus rhamnosus* strain I21 deposited under Accession No. DSM 28876.

In an embodiment, the composition can be a *Lactobacillus rhamnosus* powder. In an alternative embodiment, the composition is free of *Lactobacillus rhamnosus*.

In another embodiment, the composition can include, in addition to the metabolite of *Lactobacillus rhamnosus*, probiotic microorganisms including but not limited to *Lactobacillus* spp., *Bifidobacterium* spp., and *Saccharomyces* spp. For example, one or more of *Lactobacillus fermentum*, *Lactobacillus pentosus*, *Lactobacillus gasseri*, *Lactobacillus oris*, *Bifidobacterium longum*, and *Saccharomyces cerevisiae* can be included in the composition.

The composition can also contain one or more food ingredients, e.g., a colorant, an acidity regulator, an anticaking agent, an antioxidant, a bulking agent, a carrier, an emulsifier, a flavor enhancer, a glazing agent, a preservative, a stabilizer, a sweetener, a thickener, a nutrient additive, and a flavoring agent.

In yet another embodiment, as mentioned above, the composition includes a pharmaceutically acceptable excipient.

The composition can also be a food product. For example, the composition can be a yogurt, a beverage, an ice cream, or a cheese.

Without further elaboration, it is believed that one skilled in the art can, based on the disclosure herein, utilize the present invention to its fullest extent. The following specific examples are, therefore, to be construed as merely descriptive, and not limitative of the remainder of the disclosure in any way whatsoever.

EXAMPLES

Example 1

Lactic Acid Bacteria Produce a Xanthine Oxidase Inhibitory Activity

Thirty four lactic acid bacteria strains were separately inoculated onto De Man, Rogosa, and Sharpe (MRS) plates and cultured at 37° C. for 3 days. Bacteria strains were isolated from healthy infant feces, bovine feces, milk solids, bacon, fermented bean curd, botanical garden soil, pickles, and sauerkraut. Bacteria were scraped from each plate using a 1 μl sterile inoculation loop, inoculated into 10 ml of MRS broth, and incubated at 37° C. under facultative anaerobic conditions for 1 day to prepare an inoculum. The inoculum was then added to MRS broth at 1% (v/v) and incubated for 1 day at 37° C. under facultative anaerobic conditions. The culture medium was centrifuged and the supernatant collected for the analysis of xanthine oxidase inhibitory activity.

Xanthine oxidase inhibitory activity was measured as follows. First, 10 μl of culture media from each strain was added to a well in a 96-well plate. Then, 150 μl of 50 mM phosphate-buffered saline (PBS) and 80 μl of 150 μM xanthine was added to each well. An initial absorbance value at 290 nm ($OD_{before}$) was determined before adding 10 μl of xanthine oxidase (0.1 U) into each well. After incubating the plate at $$XOI\ (\%) = \frac{100 \times [1 - (OD_{after} - OD_{before})]}{(Blank\ OD_{after} - Blank\ OD_{before})}$$

25° C. for 30 min., the absorbance value was measured again at 290 nm ($OD_{after}$). The xanthine oxidase inhibitory activity (XOI) of each sample was calculated according to the following formula:

The results are shown in Table 1 below. Among the 34 lactic acid bacteria strains tested, two strains, namely, strains I21 and F73 (shown in italics), inhibited xanthine oxidase activity more than 40%.

TABLE 1

Xanthine oxidase inhibitory activity of lactic acid bacteria strains

| strain | E021 | E027 | E032 | E100 | E103 | E106 | E108 | E109 | E111 | E112 |
|---|---|---|---|---|---|---|---|---|---|---|
| % inh. | 8.0[a] | 20.6 | 17.4 | 7.2 | 26.2 | 25.7 | 30.0 | 8.7 | 27.8 | 32.3 |
| strain | I01 | I02 | I03 | I04 | I07 | I08 | I10 | I11 | I15 | I16 |
| % inh. | 17.6 | 10.6 | 7.0 | 1.4 | 33.6 | 20.3 | 29.4 | 2.6 | 13.9 | 2.1 |
| strain | I18 | I21 | I28 | I29 | I30 | I32 | S10-V1 | S16-6 | S16-9 | S16-10 |
| % inh. | 4.4 | 44.5 | 18.0 | 7.3 | 3.1 | 2.5 | 24.3 | 26.2 | 32.3 | 22.8 |
| strain | S17-2 | F73 | 13-2 | En3721 | | | | | | |
| % inh | 29.7 | 68.1 | 24.7 | 18.6 | | | | | | |

[a]values are expressed as percentage inhibition of xanthine oxidase activity

Example 2

HPLC Analysis of Xanthine Oxidase Activity Inhibition

Lactic acid bacteria strains F73 and I21 were inoculated onto MRS plates and cultured at 37° C. for 3 days. The bacteria were scraped from the plate with a 1 μl sterile inoculation loop, inoculated into MRS broth, and incubated at 37° C. for 1 day to prepare an inoculum. The inoculum was then added to MRS broth and incubated at 37° C. for up to 7 days. Samples were removed from the culture at day 1, day 2 and day 7, centrifuged, and the supernatant collected for the analysis of xanthine oxidase inhibitory activity.

In a reaction tube, 880 μl of xanthine (50 μg/ml in 100 mM PBS) and 40 μl of 50 mM PBS or 40 μl of the culture supernatants were premixed, and 80 μl of xanthine oxidase (0.1 U) was added to initiate the reaction. The reaction was incubated at 30° C. for 30 min., after which an equal volume of absolute ethanol was added to terminate the reaction. The terminated reaction was filtered through a 0.25 μm membrane filter and the content of xanthine was analyzed by HPLC. Xanthine oxidase inhibitory activity of the samples was calculated as follows:

$$XOI\ (\%) = \frac{100 \times [xanthine]_{initial} - [xanthine]_{after\ sample}}{[xanthine]_{initial} - [xanthine]_{after\ control}}$$

The results are shown in Table 2 below.

TABLE 2

Inhibition of xanthine oxidase activity

| strain | 1 day[a] | 2 days | 7 days |
|---|---|---|---|
| I21 | 26.74[b] | 27.39 | 24.63 |
| F73 | 14.95 | 17.23 | 23.55 |

[a]number of days in culture at which sample was removed
[b]values expressed as percentage inhibition of xanthine oxidase activity The results demonstrated that xanthine oxidase inhibitory activity of lactic acid bacteria strain I21 is higher than strain F73. Notably, the xanthine oxidase inhibitory activity of strain I21 reached a maximum after 1 day of fermentation. Prolonged culturing of strain I21 for up to 7 days did not result in an increase of xanthine oxidase inhibitory activity.

Example 3

Identification of Lactic Acid Bacteria Strain I21

Lactic acid bacteria strain I21 was isolated from the feces of a healthy infant. An analysis of this strain revealed that it was Gram-positive, catalase and oxidase negative, and non-motile. Additionally, the strain did not produce endospores and did grow under both aerobic and facultative anaerobic conditions.

The sequence of 16S rDNA from strain I21 (SEQ ID NO: 1) was analyzed and determined to be most similar to *Lactobacillus casei, Lactobacillus paracasei* subsp. *paracasei, Lactobacillus paracasei* subsp. *tolerans, Lactobacillus rhamnosus,* and *Lactobacillus zeae*. The 16s rDNA sequence similarity is as high as 98%.

An analysis of a partial sequence of the DnaK gene (SEQ ID NO: 2) revealed that strain I21 shares 99% sequence identity to *Lactobacillus rhamnosus*.

Strain I21 was also characterized with respect to the ability to ferment certain carbohydrates using the analytical profile index API® identification system. This test revealed that strain I21 is a strain of *Lactobacillus rhamnosus*.

Applicants deposited *Lactobacillus rhamnosus* strain I21 on Jun. 2, 2014 under the terms of the Budapest Treaty with the International Strain Depositary Leibniz Institute DSMZ-German Collection of Microorganisms and Cell Culture, Inhoffenstr. 7 B, D-38124 Braunschweig GERMANY. The strain was assigned Accession No. DSM 28876.

Example 4

Treatment of Experimental Uricemia

*Lactobacillus rhamnosus* I21 was inoculated on an MRS plate and cultured at 37° C. for 3 days. Bacteria were scraped from the plate using a 1 µl sterile inoculation loop, inoculated into MRS broth, and grown at 37° C. for 1 day to prepare an inoculum. The inoculum (30 ml) was then added into 3 L MRS broth in a 5 L fermenter and grown at 37° C. for 2 days. The fermentation broth was centrifuged at 3000 rpm for 15 min. The supernatant was collected and lyophilized to produce the *Lactobacillus rhamnosus* I21 fermentation product.

ICR mice were used as experimental animals. Potassium oxonate, a uricase inhibitor, was used to induce a high level of uric acid in the serum of the mice. Mice were fasted for one hour and then fed saline or potassium oxonate (400 mg/kg) via a feeding tube. After one hour, potassium oxonate-treated mice were fed saline, allopurinol (10 mg/kg), or a *Lactobacillus rhamnosus* I21 fermentation product (150 mg or 200 mg resuspended in saline per mouse) prepared as described above. Ten animals were used for each experimental group and for the control group. The animals were sacrificed after one hour and the level of uric acid in their serum was analyzed. The results are shown in Table 3 below.

TABLE 3

A fermentation product of *Lactobacillus rhamnosus* I21 can reduce serum uric acid levels in experimental animals.

| Experimental group[a] | serum uric acid concentration |
| --- | --- |
| saline control | 3.51 ± 0.02 mg/dL |
| potassium oxonate (400 mg/kg) | 4.91 ± 0.08 mg/dL |
| potassium oxonate + allopurinol (10 mg/kg) | 2.82 ± 0.28 mg/dL |
| potassium oxonate + 150 mg fermentation product | 4.00 ± 0.49 mg/dL |
| potassium oxonate + 200 mg fermentation product | 3.86 ± 0.13 mg/dL |

[a]mice (N = 10 per condition) fed saline or the compounds indicated in a total volume of 200 µl

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, a person skilled in the art can easily ascertain the essential characteristics of the present invention, and without departing from the spirit and scope thereof, can make various changes and modifications of the present invention to adapt it to various usages and conditions. Thus, other embodiments are also within the claims.

The invention claimed is:

1. A method for reducing uric acid levels in a subject, the method comprising culturing Lactobacillus rhamnosus in a medium to form a composition and administering the composition to a subject in need thereof in an amount effective for reducing uric acid levels, wherein the Lactobacillus rhamnosus is removed from the composition prior to the administering step.

2. The method of claim 1, wherein the Lactobacillus rhamnosus is Lactobacillus rhamnosus I21 deposited under Accession No. DSM 28876.

3. The method of claim 1, wherein the subject suffers from gout or hyperuricemia.

4. The method of claim 1, wherein the composition is administered orally, intramuscularly, intradermally, intravenously, subcutaneously, intraperitoneally, intranasally, or mucosally.

5. The method of claim 1, wherein the medium is de Man-Rogosa-Sharpe (MRS) broth, milk, or a juice.

6. The method of claim 1, further comprising lyophilizing the composition to form a powder.

7. A method for producing a composition for reducing uric acid levels in a subject, the method comprising inoculating a medium with Lactobacillus rhamnosus, culturing the Lactobacillus rhamnosus in the medium, removing the Lactobacillus rhamnosus from the medium to form a composition free of *Lactobacillus rhamnosus*, and lyophilizing the composition, wherein the *Lactobacillus rhamnosus* is *Lactobacillus rhamnosus* I21 deposited under Accession No. DSM 28876.

8. The method of claim 7, wherein the culturing is carried out for 2 days at 37° C.

9. The method of claim 8, wherein a culture density prior to the removing step is $1\times10^9$ cells/ml.

10. A method for producing a composition for reducing uric acid levels in a subject, the method comprising inoculating a medium with *Lactobacillus rhamnosus*, culturing the *Lactobacillus rhamnosus* in the medium, removing the *Lactobacillus rhamnosus* from the medium to form a composition free of *Lactobacillus rhamnosus*, and sterilizing the composition by pasteurization, irradiation, autoclave, or filtration, wherein the *Lactobacillus rhamnosus* is *Lactobacillus rhamnosus* I21 deposited under Accession No. DSM 28876.

* * * * *

```
                        SEQUENCE LISTING

<160> NUMBER OF SEQ ID NOS: 2

<210> SEQ ID NO 1
<211> LENGTH: 1537
<212> TYPE: DNA
<213> ORGANISM: Lactobacillus rhamnosus
<220> FEATURE:
<221> NAME/KEY: misc_feature
<223> OTHER INFORMATION: strain I21 16s rDNA

<400> SEQUENCE: 1
tcaggatgaa cgctggcggc gtgcctaata catgcaagtc gaacgagttc tgattattga      60
aaggtgcttg catcttgatt taattttgaa cgagtggcgg acgggtgagt aacacgtggg     120
taacctgccc ttaagtgggg gataacattt ggaaacagat gctaataccg cataaatcca     180
agaaccgcat ggttcttggc tgaaagatgg cgtaagctat cgcttttgga tggacccgcg     240
gcgtattagc tagttggtga ggtaacggct caccaaggca atgatacgta gccgaactga     300
gaggttgatc ggccacattg ggactgagac acggcccaaa ctcctacggg aggcagcagt     360
agggaatctt ccacaatgga cgcaagtctg atggagcaac gccgcgtgag tgaagaaggc     420
tttcgggtcg taaaactctg ttgttggaga agaatggtcg cagagtaac tgttgtcggc      480 gtgacggtat ccaaccagaa agccacggct aactacgtgc cagcagccgc ggtaatacgt     540
aggtggcaag cgttatccgg atttattggg cgtaaagcga gcgcaggcgg ttttttaagt     600
ctgatgtgaa agccctcggc ttaaccgagg aagtgcatcg gaaactggga aacttgagtg     660
cagaagagga cagtggaact ccatgtgtag cggtgaaatg cgtagatata tggaagaaca     720
ccagtggcga aggcggctgt ctggtctgta actgacgctg aggctcgaaa gcatgggtag     780
cgaacaggat tagataccct ggtagtccat gccgtaaacg atgaatgcta ggtgttggag     840
```

```
ggtttccgcc cttcagtgcc gcagctaacg cattaagcat tccgcctggg gagtacgacc      900
gcaaggttga aactcaaagg aattgacggg ggcccgcaca agcggtggag catgtggttt      960
aattcgaagc aacgcgaaga accttaccag gtcttgacat cttttgatca cctgagagat     1020
caggtttccc cttcggggc aaaatgacag gtggtgtatg gttgtcgtca gctcgtgtcg      1080
tgagatgttg ggttaagtcc cgcaacgagc gcaacccta tgactagttg ccagcattta      1140
gttgggcact ctagtaagac tgccggtgac aaaccggagg aaggtgggga tgacgtcaaa     1200
tcatcatgcc ccttatgacc tgggctacac acgtgctaca atggatggta caacgagttg     1260
cgagaccgcg aggtcaagct aatctcttaa agccattctc agttcggact gtaggctgca     1320
actcgcctac acgaagtcgg aatcgctagt aatcgcggat cagcacgccg cggtgaatac     1380
gttcccgggc cttgtacaca ccgcccgtca caccatgaga gtttgtaaca cccgaagccg     1440
gtggcgtaac ccttttaggg agcgagccgt ctaaggtggg acaaatgatt agggtgaagt     1500
cgtaacaagg tagccgtagg agaacctgcg gctggat                              1537

<210> SEQ ID NO 2
<211> LENGTH: 792
<212> TYPE: DNA
<213> ORGANISM: Lactobacillus rhamnosus
<220> FEATURE:
<221> NAME/KEY: misc_feature
<223> OTHER INFORMATION: strain I21 partial DNAK sequence

<400> SEQUENCE: 2
agatgcggtt atcacagttc cggcttactt taacgacagt cagcgtcagg caaccaagga       60
tgccggtaag atcgctggtt tgaatgttca acggattatc aacgaaccaa ccgcgtcagc      120
cttggcttat ggtctggata aaggcgacaa agacgaaaag attttggttt acgaccttgg      180
cggcgggaca tttgatgttt ccatcctgca gttaggtgat ggtgtcttcg aagtgctgtc      240
aaccaatggc gatactcatt taggcgggga tgattttgat aacaagatca tcgactggct      300
tgtttccgaa ttcaaaaagg ataacaacat tgacctgtct aaagacaaaa tggcaatgca      360
acgcctgaag gatgcagccg aaaaagctaa gaaggatctt tccggtgtga cccagacgca      420
aatcagcttg ccatttattt ctgccggccc caacggccca ttgcacttgg aacgcacttt      480
aacccgtgca caatttgacg aaaatgaccgc cgacttggtt gctaagacca aggtgccagt      540
tgaaaatgcg ctgaaagatg ctaaattgac gaaagcagat attgacaaag taatcttaaa      600
tggtggttca acacggatcc ctgctgttca acaagcagtt aaaggaatgg actggcaaag      660
atccggacca cagcatcaac ccagacgaag cggttgcgct aggtgctgcc gttcagggtg      720
gtgtcatttc cggtgacgtg aaggatgttg ttttgctgga tgttacgccg ctgtcattag      780
ggattgaaac ca                                                         792
```